(12) United States Patent
Fang et al.

(10) Patent No.: US 12,276,662 B2
(45) Date of Patent: Apr. 15, 2025

(54) DEVICE FOR ANALYTE ASSAYS WITH BUILT-IN RESULT REPORTING USING RECOGNIZABLE SYMBOLS

(71) Applicants: Zhejiang Orient Gene Biotech Co., Ltd, Zhejiang (CN); Healgen Scientific Limited, Houston, TX (US)

(72) Inventors: Jianqiu Fang, Zhejiang (CN); Xiulong Ge, Zhejiang (CN); Chunmei Zhong, Zhejiang (CN); Fangzhou Xu, Zhejiang (CN)

(73) Assignees: Zhijiang Orient Gene Biotech Co., Ltd, Huzhou (CN); Healgen Scientific Limited, Houston, TX (US)

( * ) Notice: Subject to any disclaimer, the term of this patent is extended or adjusted under 35 U.S.C. 154(b) by 788 days.

(21) Appl. No.: 17/500,472

(22) Filed: Oct. 13, 2021

(65) Prior Publication Data

US 2022/0128554 A1    Apr. 28, 2022

Related U.S. Application Data

(60) Provisional application No. 63/107,423, filed on Oct. 29, 2020.

(30) Foreign Application Priority Data

Oct. 23, 2020    (CN) .......................... 202011145454.X (51) Int. Cl.
*G01N 1/00*    (2006.01)
*G01N 33/543*    (2006.01)

(52) U.S. Cl.
CPC .............................. *G01N 33/54388* (2021.08)

(58) Field of Classification Search
CPC ............ G01N 33/54388; G01N 21/84; G01N 33/543; G01N 33/558
See application file for complete search history.

(56) References Cited

U.S. PATENT DOCUMENTS

2006/0029924 A1*    2/2006    Brewster .................. C12Q 1/00
435/4

FOREIGN PATENT DOCUMENTS

| CN | 1682114 A | 10/2005 | |
| CN | 110057819 A | 7/2019 | |
| CN | 210142078 U | * 7/2019 | ............. G01N 21/84 |

* cited by examiner

*Primary Examiner* — Jyoti Nagpaul
(74) *Attorney, Agent, or Firm* — NZ Carr Law Office (57) ABSTRACT

A device for indicating a test result of a specimen using recognizable symbols includes a reagent strip, wherein the reagent strip includes a detection zone including an analyte binding area and a positive control area, and the positive control area includes a first-layer reagent and a second-layer reagent; the first-layer reagent is a reagent that becomes transparent when exposed to water, the second-layer reagent is a colored reagent, and the first-layer reagent is not transparent when dry but becomes transparent when wetted; or a device for indicating a test result of a specimen using recognizable symbols, which includes a reagent strip, and the reagent strip includes a detection zone including an analyte binding area and a positive control area; wherein the positive control area includes a light-emitting element which emits light after energizing, and the light emitted by the element is projected to the positive control area.

24 Claims, 5 Drawing Sheets

DEVICE FOR ANALYTE ASSAYS WITH BUILT-IN RESULT REPORTING USING RECOGNIZABLE SYMBOLS

CROSS-REFERENCE TO RELATED APPLICATION

This application claims the priority of the following prior applications, a prior Chinese patent application 202011145454.X, filed on Oct. 23, 2020, and a U.S. prior provisional application 63/107,423, filed on Oct. 29, 2020. The entirety of which is incorporated herein by reference.

TECHNICAL FIELD

The present invention belongs to medical diagnostic products, in particular to an assay device that can quickly detect presence of an analyte in a sample.

BACKGROUND

The inclusion of positive and negative control tests in the performance of an assay is considered an important component of an assay. In immunological test, the control tests are often performed by following the principle of immunity to form a control, and the result of the control test can be displayed as a colored line on the test strip. The control tests are effective for verifying that the assay device is functioning correctly, but they also result in added expense in making the device and performing the assay, particularly when the specific binding molecules used in the control tests are produced as a result of elaborate procedures. Additionally, these types of the control tests can be confusing for the untrained general consumer and lead to improper test interpretation. There is therefore a need for better methods and devices for performing sample collection and testing, to provide more intuitive test results, which can be properly interpreted by untrained general consumers.

There are similar patent applications on the test results via visual display, for example, U.S. Patent U.S. Pat. No. 7,704,753 also describes the test results via visual display, but such kind of visual symbol is a positive control area, and the positive control area is similar to a bibulous strip where a color reagent is processed. But such kind of positive control area has high processing difficulty and more complex process. For another example, U.S. Patent U.S. Pat. No. 7,803,636B2 discloses a similar description. But in the application, the positive control area is covered by a water-soluble dye, and the water-soluble dye may change color, which is demanding for a higher process requirement of a processing membrane, and has difficulty in processing.

Therefore, a different solution needs to be provided to achieve a device which is easy to be processed and produced in large scale, and capable of displaying a test result visually.

SUMMARY

The present invention provides a device for detecting the presence of an analyte in a liquid sample, which can indicate the presence of the analyte with a recognizable symbol for a user.

On the one hand, in a detailed embodiment, the present invention provides a reagent strip, including a detection zone, and the detection zone includes an analyte binding area and a positive control area. The analyte binding area and the positive control area are combined into a recognizable symbol to indicate a test result.

In some embodiments, the positive control area includes a first element and a second element, where the first element becomes transparent when exposed to water; and the second element is colored. In some embodiments, the first element is not transparent when dry but becomes transparent when wetted. In this way, the color of the second element is displayed.

In some embodiments, the first element is covered on the second element; when the first element becomes transparent when wetted from a non-transparent state when dry, the color of the first element is displayed, thus being combined with the analyte binding area into a recognizable symbol.

In some embodiments, the first element is covered on the second element. In some embodiments, the first element is a layer of reagent, and the reagent is not transparent when dry but becomes transparent when wetted. Moreover, the reagent may not flow with liquid, and is basically in a fixed state. The main reason why the reagent on the first element is kept in a fixed state is that a biological reagent, for example, an antibody or an antigen is treated in the analyte binding area, such that some chemical reactions perform thereon. If the reagent in the positive control area flows with liquid, the reagent may flow onto the nearby analyte binding area to affect the chemical reaction in the analyte binding area, thus influencing the final test result. The reaction in the analyte binding area refers to a binding reaction between antibodies, or an antibody and an antigen. This because the analyte binding area and the positive control area need to be combined into a recognizable symbol; therefore, the two area are generally close to each other, and maybe, there exists an overlapped area. In this case, it is desirable that the chemical reaction of the positive control area is free of influencing that of the analyte binding area, or both are not mutually influenced, thus achieving an independent and non-interference ideal state. But if the reagent in the positive control area may be flowable, or some flowable reagents are covered, these reagents may flow onto the analyte binding area, thereby influencing the chemical reaction in the analyte binding area. For example, some oil-based ink are treated in the positive control area, and these ink are chemical reagents and sometimes are volatile reagents and thus, are harmful to the chemical reaction in the analyte binding area. Therefore, a flowable or movable reagent in the positive control area should be reduced as much as possible to decrease the adverse effect on the analyte binding area.

In some embodiments, the positive control area includes a film, and the film is not transparent when dry but becomes transparent when wetted. At this time, the first element may be a layer of film instead of a reagent; when the film becomes transparent in a wetted state from non-transparent in a dry state, the color area covered under the film will be displayed, such that the color area is combined with the analyte binding area into a recognizable symbol. Such kind of solution belongs to a physical process, which may effectively prevent the chemical reaction in the positive control area from being influenced by the chemical reaction in the analyte binding area, thereby obtaining a correct test result.

In some embodiments, the second element may be a chemical reagent, for example, an oil-based ink; the ink has a certain degree of color and always keeps a stable color, and has no change in color due to a dry or wetted state. In another embodiments, the second element is a colored dye, or the second element is a colored strip bonded on the detection zone. To sum up, the second element keeps a same color. The reason why the color of the positive control area in the detection zone is displayed is because the first element covered over the second element is transparent or not transparent, thus judging whether the second element is shielded or displayed. Certainly, if the second element is in a form of electronic element, the second element also develops color from nothing, but the color developing belongs to an electrophysics mode instead of chemical reaction.

In some embodiments, the analyte binding area includes a binding molecule able to capture the analyte, and also a labeled analyte. The analyte binding area and the positive control area interact to produce recognizable symbols, which can indicate the test result.

One embodiment is that the positive control area is displayed by "–" in the reagent strip, and the control area includes a first-layer reagent and a second-layer reagent, where the first-layer reagent is a reagent that may not flow with a liquid, and the second-layer reagent is a colored reagent; the first-layer reagent is not transparent when dry but becomes transparent when wetted in order to show the second-layer reagent. In some embodiments, the first-layer is covered on the second-layer. In the specific embodiment, the test strip is dry at the beginning of analysis, and the positive control area and test strip are both white or colorless. Hence, the positive control area is not visible when the detection zone is observed before adding a sample. When a liquid sample is added, the sample flows through the detection zone of the reagent strip to make the positive control area become wet, so that the positive control area changes from white or transparent to other colors, thus showing the colored area covered underneath. The colored area may be in red, blue, black or any other color. In this way, the "–" in the detection zone is clearly observed. If there is no presence of an analyte in the sample, only "–" is displayed in the detection zone, indicating a negative test result for the user. However, if the sample includes the analyte, the labeled analyte is captured by the binding molecules in the analyte binding area and accumulated continuously to show a color, the color of the analyte binding area and the minus sign (in positive control area) may interact with each other to generate a "+", indicating a positive test result for the user. The report symbol may be any recognizable symbol. For example, "+" and "–" signs can also be "X" or other symbols having a special meaning. During such a detection process, the composition of symbols and the color display in the analyte binding area is a dynamic process, rendering the symbols more clear and reliable.

In some embodiments, the device further includes a sample receiving region and a reagent zone. The detection zone includes an analyte binding area and a positive control area. The reagent zone is located on the upstream of the detection zone. The sample receiving region is located on the upstream of the reagent zone.

Therefore, the present invention provides a device for detecting presence of an analyte in a sample. The device includes a reagent strip that allows a liquid sample to flow on freely; a sample application zone specially used for adding a liquid sample; and a detection zone which includes a positive control area; where the positive control area includes a first-layer reagent and a second-layer reagent, where the first-layer reagent is a reagent that becomes transparent when exposed to water, the second-layer reagent is a colored reagent, and the first-layer reagent is not transparent when dry but becomes transparent when wetted in order to show the second-layer reagent; and the first-layer reagent is covered on the second-layer reagent. The detection zone also has an analyte binding area including specific binding molecules. The device also has one or more reagent zones for conducting the assay.

In one specific embodiment, the first reagent is a colorless or pale-colored basic dye containing one or more compositions. The reagent strip may be a nitrocellulose test strip, and the positive control area may be indicated by a minus sign on the test strip. The analyte binding area can be divided into two areas, which include molecules or molecular combinations that specifically bind to the analyte, and the two areas are configured on both sides of the positive control area. The two areas should be arranged reasonably so that when the positive control area becomes wet (the first-layer reagent becomes transparent, showing that the second-layer colored reagent) and the analyte is present in the sample, the positive control area and the analyte binding area can form a recognizable symbol. The recognizable symbol may be a plus sign or any other recognizable symbols.

In another specific embodiment, the positive control area is located on the nitrocellulose film, the first-layer reagent is ink that becomes transparent when exposed to water, and the second-layer is colored ink; when it is dry, the first-layer ink is not transparent so it covers the colored ink; when the first-layer ink becomes transparent after exposed to water, the second-layer colored ink is shown. The specific binding molecule may be an antibody or an antibody fragment. In one specific embodiment, the analyte is a human chorionic gonadotropin (hCG). The positive control area can be combined by one or more positive control areas and the analyte-specific bonding areas in the detection zone, and the positive control area does not have many components for specific binding.

In another specific embodiment, the analyte binding area further includes specific binding molecules to bind to the analyte, and also a label of a signal which can be detected. The label may be a colored particle, for example a particle containing dextran. The analyte binding area can be present as a bar situated latitudinally along the central axis of the test strip, and may include binding molecules that can specifically bind to the analyte. The positive control area may be composed of two areas located on both sides of the analyte binding area. The positive control area and the analyte binding area may interact to form a recognizable symbol.

In some embodiments, the second element is colored, and such kind of color may be a constant color. Since the first element is covered on the second element, the fixed color of the second element is displayed due to the change of the first element, for example, changing from non-transparent in the dry state to transparent in a wetted state. Certainly, in some examples, the second element may change in color, and such kind of change may be correlated or not correlated to a wetted state. When correlated to a wetted state, the second element may be also colorless dry but becomes colored when wetted. When the change of color is little correlated to moisture, namely, the second element will emit light when energized mentioned hereafter, such kind of light is colored, for example, the second element is a light-emitting element itself, and the element emits no light when not energized, but emits light when electrified. Such kind of light may be a monochromatic light, for example, a red light, a blue light, or any other color of lights, and may be certainly a mixed light, and such kind of light is projected to the positive control area to form a colored positive control area. Of course, the shape of the light-emitting element is matched with that of the positive control area, for example, when the positive control area shows "–", the width and length of the light-emitting element may be the same as those of the "–". How to form a recognizable symbol with the analyte control area to display the test result when the positive control area is a light-emitting element will be described in detail hereafter.

On the other hand, the present invention provides a method for detecting presence of an analyte in a liquid sample. The method includes the following steps: place the liquid sample on a device according to the method described therein, and make the liquid sample flows through the device and one or more reagent zones, so that if the analyte present in the sample, the reagent and the sample can react to product a detectable reaction product. The first element is wet when the liquid sample flows through the detection zone, thereby changing from non-transparent to transparent, and showing the second element covered under the first element, displaying the original color of the second element, or making the second element colored. The analyte in the sample is retained in the analyte binding area when the sample flows through the detection zone. Presence of an analyte in the liquid sample can be determined by observing the detection zone of the device.

In another specific embodiment, the analyte in the sample is labeled with a detectable label when passing through the reagent zone, and the labeled analyte is retained in the analyte binding area when the sample passes through the detection zone.

On the other hand, the present invention provides a kit to determine presence of an analyte in a sample. As described herein, the kit includes a device of the invention and the operating instructions. The test device in the kit can be used to detect HCG in a urine sample. In another specific embodiment, the device is also used to detect luteinizing hormone (LH) or ovarian stimulating hormone (FSH) in a body liquid and the operating instructions in the kit describes how to use the device to detect the substances.

Besides, in one specific embodiment provided by the present invention, a reagent strip is disclosed, including a detection zone. The detection zone includes an analyte binding area and a positive control area. The positive control area has a light-emitting element which can emit light. In some embodiments, the light-emitting element is a colored light source element, and the light source element shows color when energized, but shows no color or white when de-energized, that is to say, the light source element shows color when a current passes through. The color here is generally a monochromatic light, for example, red fluorescence or blue fluorescence, or monochromatic light displayed by a LED tube, for example, a red light or blue light. The analyte binding area includes a binding molecule able to capture the analyte, and also a labeled analyte. The analyte binding area and the positive control area interact to produce recognizable symbols, which can indicate the test result.

One specific embodiment is that the positive control area is displayed by "−" in the reagent strip, and the control area includes a colored light source element. The light source element is shows color when energized, but shows no color when de-energized, that is to say, the light source element shows color when a current passes through. For the convenience of achieving the simultaneous implementation of the energizing status of the positive control area and the detection/assay of the analyte binding area, thus controlling the practical energized condition of the light-emitting element, a form of fluid conduction may be taken. For example, a light-emitting element is arranged in the detection zone to be combined with an analyte into a shape; a power supply is arranged in a concealed area, for example, a button cell or other power supplies, and the power supply is connected with the light source via a lead wire, where, the positive pole and negative pole (live line or null line) of the lead wire are arranged on the sample application zone or the reagent zone of the test strip; the positive wire is not in conduction with the negative wire, namely, not in a connection mode. When a liquid sample is applied, the liquid sample flows on the sample application zone or reagent zone, thus conducting the positive pole and negative pole to form a current loop, such that the light-emitting element emits light and the color of the positive control area is displayed.

There are multiple modes of displaying color; in some embodiments, when the shape or size of the light-emitting element is the same as that of the positive control area, the light emitted by the light-emitting element or color displayed is the same as that of the positive control area, and the positive control area has a colored symbol. In some embodiments, the light emitted by the light-emitting element is generally scattered and thus, is hardly controlled in its shape. Therefore, it is difficult to control a specific shape. If it is desirable to form a preset shape, light may transmit through a conversion element to be converted into a fixed shape, for example, rectangle, round, or other any shapes of letters. For example, a conversion element is set between a light source and the positive control area, such that the ray of light is converted into a preset shape via the conversion element. For example, a conversion element similar to a concave lens or a convex lens, a ray of light forms a fixed shaped via these lens; or the conversion element is from some light-proof elements; and some hollow structures are set on these light-proof elements, and these hollow structures have a fixed shape, and the hollow shape is namely the shape of the positive control area. In this way, a symbol defined by the hollow structure is projected on the positive control area, thus being combined with the analyte binding area into a recognizable symbol. For example, the hollow shape is "−", or any other shapes, for example, partial symbols of "Y", or the like.

In the specific embodiment, the test strip is dry at the beginning of analysis, and the positive control area and test strip are both white or colorless. Hence, the positive control area is not visible when the detection zone is observed before adding a sample. When a liquid sample is added, the liquid is connected to the power supply circuit, and power is supplied to the light-emitting element, emitting a colored light. The color may be red, blue, black or any other. In this way, the "−" in the detection zone is clearly observed. If there is no presence of an analyte in the sample, only "−" is displayed in the detection zone, indicating a negative test result for the user. However, if the sample includes the analyte, the labeled analyte is captured by the binding molecules in the analyte binding area and accumulated continuously to show a color, the color of the analyte binding area and the minus sign (in positive control area) may interact with each other to generate a "+", indicating a positive test result for the user. The report symbol may be any recognizable symbol. For example, "+" and "−" signs can also be "X" or other symbols having a special meaning.

First, the present invention provides a device for detecting presence of an analyte in a sample. The device includes a reagent strip that allows a liquid sample to flow on freely; and a sample application zone specially used for adding a liquid sample; the sample application zone is connected to a positive and negative poles of the power supply, so that a current circuit is formed when a liquid passes through, thus to supply power to the light-emitting element and make the element emit a colored light, for example red light or blue light. The detection zone also has an analyte binding area including specific binding molecules. The device also has one or more reagent zones for conducting the assay.

In one specific embodiment, the reagent strip may be a nitrocellulose test strip, and the light source or light-emitting element in the positive control area can be under the nitrocellulose film in the form of a minus sign, for example, a 4-5 mm long light-emitting element, with a diameter of 2 mm. The analyte is bound at the nitrocellulose film as it includes molecules or molecular combinations that specifically bind to the analyte, and a plus sign may be formed if the binding area is located in the positive control area. In this way, when applied to the sample area, a liquid makes the electricity conducted, so that the light-emitting element shows a color;

after the liquid flowing onto the nitrocellulose film, the film becomes transparent when exposed to water, and the light emitted from the light-emitting element is thus displayed to expose the light-emitting element below itself, thereby becoming visible in the form of a minus sign. If the analyte is present in the sample, the positive control area and the analyte binding area can form a recognizable symbol. The recognizable symbol may be a plus sign or any other recognizable symbols. If the sample contains no analyte, the positive control area is only displayed in the form of a minus sign, indicating that the result is negative.

In one specific embodiment, the analyte is a human chorionic gonadotropin (hCG). The positive control area can be combined by one or more positive control areas and the analyte-specific bonding areas in the detection zone, and the positive control area does not have many components for specific binding.

In another specific embodiment, the analyte binding area further includes specific binding molecules to bind to the analyte, and also a label of a signal which can be detected. The label may be a colored particle, for example a particle containing dextran. The analyte binding area can be present as a bar situated latitudinally along the central axis of the test strip, and may include binding molecules that can specifically bind to the analyte. The positive control area may be composed of two areas located on both sides of the analyte binding area. The positive control area and the analyte binding area may interact to form a recognizable symbol.

In some other embodiments, a light source conversion element is provided under the nitrocellulose film, and the light source conversion element includes a conduction channel which includes a light outlet and inlet; electronic luminescent elements are arranged in the conduction channel, such as a LED lamp, a fluorescent element; and these elements emit light after energized, and the light is transmitted or displayed from the outlet. The outlet may be shaped in any form; the light transmitted from the designed outlet is projected onto the nitrocellulose film to form symbols consistent with the shape of the outlet, and these symbols are displayed on the nitrocellulose film. The emitted light irradiates on the nitrocellulose film, projected in a certain shape on the film. An analyte binding area is arranged on the film, which forms a certain symbol with the light outlet. When the analyte is present in the sample, it indicates a positive symbol; when the analyte is not present in the sample, it indicates a negative result. During operation, the liquid sample is made to flow onto the test strip to form a current circuit, so that the light-emitting element emits light, and the light emitted is projected onto the film or behind the film through the light outlet. After wet by the liquid, the film becomes transparent and visible; if the analyte is present in the sample, it will accumulate in the analyte area and show color, thus being combined with the positive control projected on the film to show the symbol of a positive result; if otherwise, only the optical shape of the positive area is displayed, thereby indicating a negative result. The shape of the light outlet may vary in any way, for example, a thin rectangle, with the length and width equal to that of the analyte binding area, but forming a "+" shape when crossing with the analyte binding area. The light projected on the film can be projected to the back of the film or from the front of the film, thus to combine with the analyte area to form a symbol.

The combination of the shape of the light projected to the film and the analyte binding area can be set arbitrarily, the projection shape may be determined by the shape of the light-emitting element itself, for example, a thin rectangle, a cylinder and a circle. When the light-emitting element is directly arranged under the film, and the shape of the light-emitting element itself is displayed under the film. In another embodiment, the light emitted by the light-emitting element is projected onto the film through a light outlet, while the shape of the light outlet determines the shape of the light projected on the film. For example, the light emitted by a light source is projected onto the film through a light outlet of the channel, and the light outlet is rectangle, and an opening of the rectangle has the same size as the analyte binding area, or combines with the analyte area to form a certain shape; the combination shape is a positive symbol if the result is positive; and the combination shape is a negative symbol if the result is negative, thus suggesting different meanings of results.

In further some embodiments, a light source is arranged into a box which is light-proof all around, and the box is provided with some hollow structures; these hollow structures allow light to pass through, thus being irradiated or projected on the nitrocellulose film. The ray of light cannot transmit through the film when the nitrocellulose film is dry and not transparent, and when the film becomes transparent, the light passing through the hollow structures is projected to the film or the hollow shape is displayed from the transparent nitrocellulose film, thus being combined with the analyte binding area into specific symbols, indicating the test results. At this time, the light-emitting element gives off light by energization. The light-emitting element is not in a specific shape, but only plays a light-emitting role, for example, the role of homogeneous light or scattered light, and thus a conversion element is required. Further, the conversion element is provided with a symbol required by the positive control area, for example, a form of "−", thus achieving the display of the symbol. The symbol is combined with the analyte binding area to form a directly recognizable symbol, thus displaying the test result.

In another specific embodiment, the analyte in the sample is labeled with a detectable label when passing through the reagent zone, and the labeled analyte is retained in the analyte binding area when the sample passes through the detection zone.

The descriptions given above are not a full introduction of the present invention, and other features and advantages of the present invention will be elaborated in the following descriptions and statements.

BRIEF DESCRIPTION OF THE DRAWINGS

FIG. 1 depicts a perspective view of one embodiment of a device of the present invention, including a reagent strip 10. The reagent strip 10 includes a sample detection zone 108, wherein the detection zone includes an analyte binding area 101 and a positive control area 102 crossed with the analyte binding area, the positive control area includes a first element 1020 that is not transparent when dry and becomes a transparent ink when wetted, and a layer of colored ink 105 covered under the first element. The positive control area and the analyte binding area are combined to form a form of a plus "+" sign.

FIG. 2 depicts a top view of one embodiment of the present invention. The positive control area 105 displays the shape of a minus sign, which can be engraved on a nitrocellulose film, or printed, painted or drawn on the nitrocellulose film.

DETAILED DESCRIPTION OF THE EMBODIMENTS

In the following detailed descriptions, the reference text attached to the legend represents a part, and it illustrates the specific embodiments of the present invention by examples. It is not excluded that the present invention implements other specific embodiments and the structure of the present invention without departing from the use scope of the present invention.

Assay Device

In one embodiment, the device of the present invention uses a test strip to detect a presence of an analyte in a liquid sample. The devices convey the test results to the user in the form of recognizable symbols, and the recognizable symbols are formed by combination of the visual signals generated by the positive control area and the analyte binding area.

Figure 1:
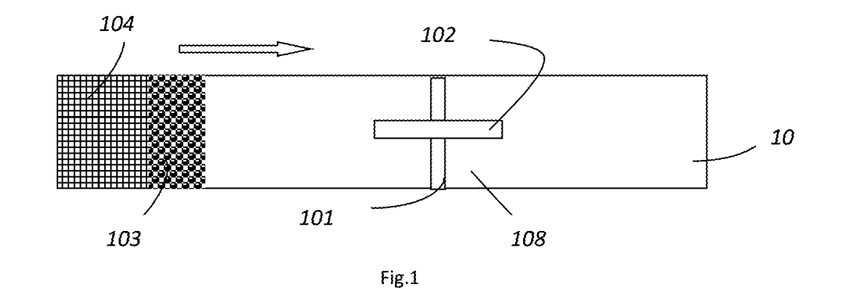
Figure 2:
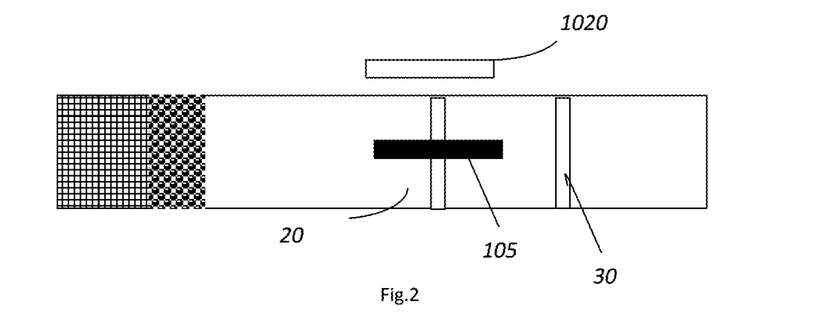
Figure 3:
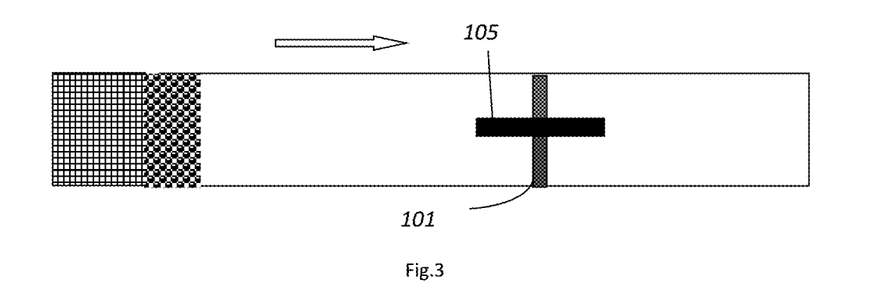
FIG. 3 is an analysis diagram of another embodiment of the present invention, the analyte binding area is combined with the positive control area into a "+" symbol to indicate a positive result when a color is displayed in the analyte binding area, and the reverse combination shows a "−" symbol to indicate a negative result.

FIGS. 1-3 depict one embodiment of the device. The assay device includes a reagent strip 10 that allows liquid samples to flow through. The reagent strip includes a sample application zone 104 for applying a liquid sample to the device, a reagent zone 103 and a detection zone 108. The reagent zone 103 includes a reagent used for the test. The test strip may have more than 1 reagent zone according to the requirements of a specific test. The detection zone 108 includes a positive control area 102, an analyte binding area 101 and a negative control area 30. The negative control area does not display color when the test is conducted normally. In the specific embodiment, the negative control area 30 is easily indicated by those areas surrounding the plus sign, because those areas surrounding the plus sign will show a plus sign when an analyte is present in the sample (for example, when plus sign is selected as a recognizable symbol).

Figure 4:
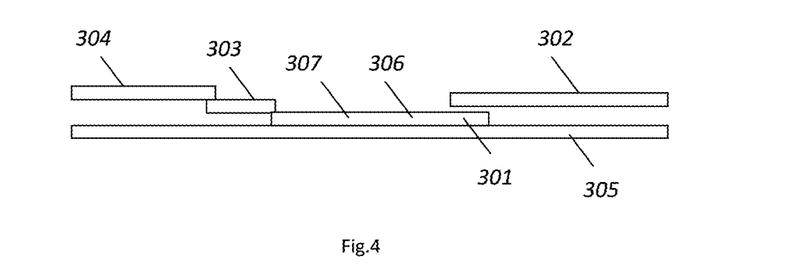
FIG. 4 is a structure diagram of a reagent strip, including a sample application zone 304 for receiving a fluid sample, a reagent zone 303, a film 301 containing a detection zone 307 and a result control area 306, and a bibulous zone 302, where these zones are located on a supporting element 3-5.
Figure 5:
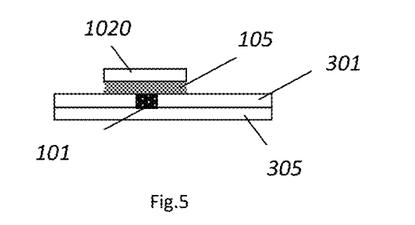
FIG. 5 is a sectional drawing of a specific embodiment as shown in FIG. 1, where the analyte binding area is located on the film 301, and the positive control area 102 is also located on the film; the positive control area includes a first element 102 and a second element 105 covered by the first element; the second element is colored; the first element is not transparent when dry, but transparent when wetted.
Figures 6, 7A, 7B, 7C:
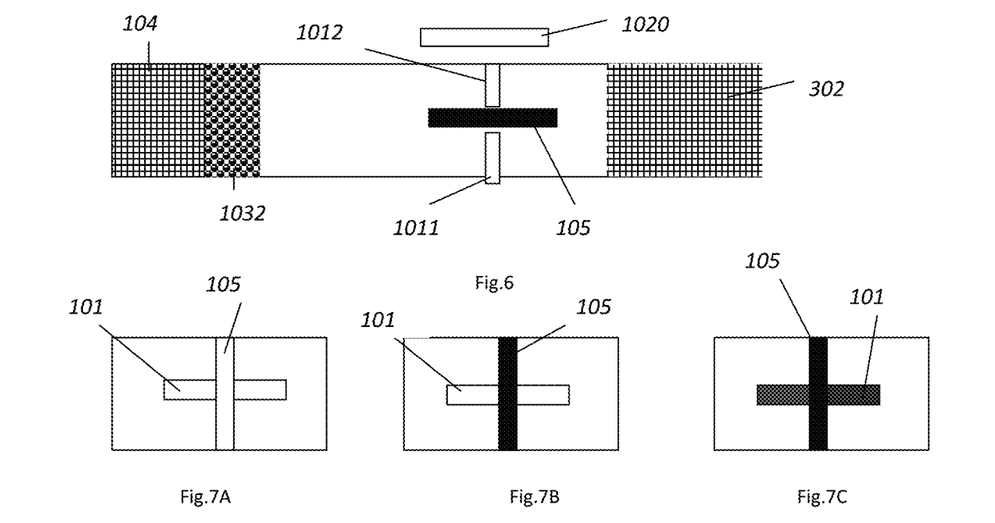
FIG. 6 is a schematic diagram of another example of the present invention, where the positive control area and the test strip are distributed longitudinally, and the analyte binding area is respectively located at both sides of the positive control area, thus being combination into a shape.
FIGS. 7A-7C shows a display process of a positive result that a positive control area is vertical to the overall direction of a test strip, and an analyte binding area is distributed in longitudinal parallel to the test strip in an example.
Figure 8:
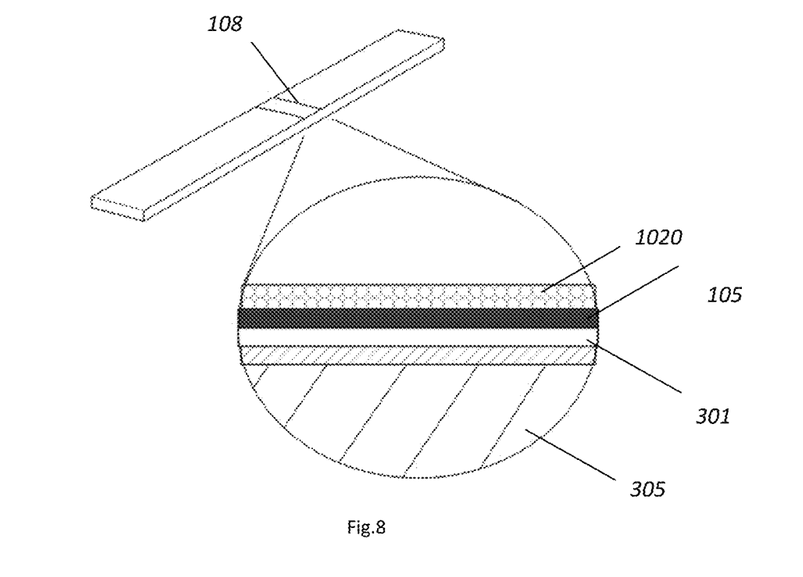
FIG. 8 is a schematic diagram showing a sectional structure of a positive control area on the test strip 10.
Figure 9:
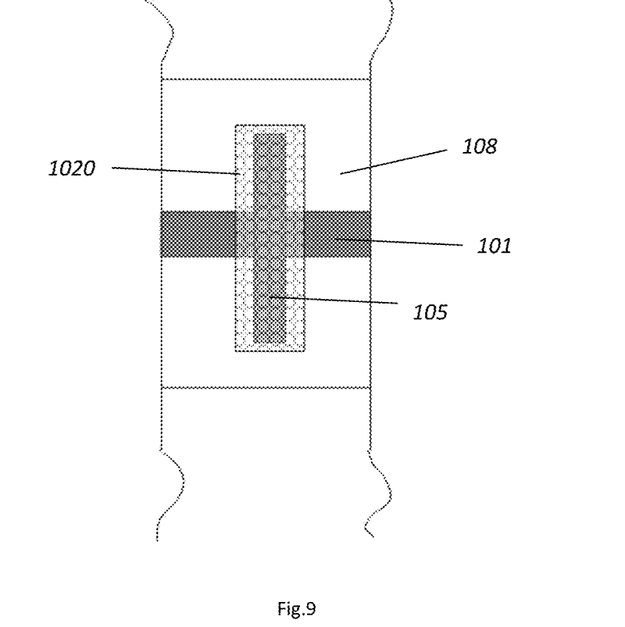
FIG. 9 shows a top view in a detailed embodiment of the present invention.

FIGS. 4 and 5 depict one embodiment of the device. In the specific embodiment, the reagent strip 300 is composed of multiple overlapping materials, including a sample application zone 304, a reagent zone 303, a nitrocellulose strip 301 and an absorption area 302. nitrocellulose. The detection zone 108 is arranged on the nitrocellulose strip. The positive control area 102 and the negative control area 306 are in the detection zone. The absorption area 302 provides a liquid sample absorption and reception area, so it can promote the liquid to flow through the test strip until the end of the test. In various specific embodiments, the each zone/area of the test strip can be bonded together with one or more adhesive substances (not illustrated). For example, bonded on a supporting piece 305 to constitute a complete test strip. For example, FIG. 5 is a schematic diagram showing a sectional structure of one embodiment; the supporting piece 305 is provided with a film, for example, a nitrocellulose film 301 which is provided with a detection zone 108; the detection zone includes an analyte binding area, for example, a T line area 101 and a positive control area 102, and the area includes a colored area 105 which will not change with the change of the dry/wet state, namely, the color keeps constant and stable. A layer of element 1020 is covered on the positive control area, and the layer may be a film or an ink which is not enough transparent when dry to make the second-layer developing color, but is transparent when wetted to display the second layer covered therebelow (FIGS. 9 and 8). In another specific embodiment of the present invention (FIGS. 1-2), the positive control area includes two layers of reagents, a first-layer reagent and a second-layer reagent, where the first-layer reagent covers the first-layer reagent, and the first-layer reagent is not transparent when dry, and becomes transparent when wetted; the second-layer reagent is colored, while it can be colorless when dry; and becomes colored when wetted. In some embodiments, for example, the first-layer is wet and transparent ink, and is not transparent when dry; and the second-layer can be colored ink or the ink that changes color when wetted. When a detection zone of a test strip is prepared, the analyte binding area 101 is fixed with an antibody or antigen which can bind to the analyte, as a vertical line for the test strip; a colored ink is treated in a position of the positive control area 102, similar to a minus "–" form, is longitudinally parallel to the test strip; and then, a layer of ink is treated above the colored ink to cover the colored ink below; the first layer of ink is kept stationary, and the ink is not transparent when dry, for example, white, and but transparent when wetted; when there is no liquid for detection, the ink is white on the detection zone, and no symbol is visible. During operation, when a liquid sample is dropwisely added to the test strip, for example, the sample application zone 104, after the liquid sample flows to the detection zone via an actual area 103, the first-layer reagent becomes transparent when it exposed to water, then the color of the second-layer reagent covered underneath is displayed (FIG. 3); if the analyte is not present in the sample, no color symbols gather in the analyte binding area, and only the positive control area is displayed, for example by a "–" sign, indicating a negative result. When the analyte is present in the sample, the analyte area also displays a color and combines with the positive control area to form a symbol to indicate a positive result, i.e. "+" (FIG. 3). The reason why the analyte displays a color is because a colored substance is treated in the reagent zone, and the substance may specifically bind to the analyte, for example, an antibody. Before the sample is tested, the analyte area does not display any color, and the positive control area, covered by a white ink, also becomes white. At this time, the ink in the positive control area may not flow with liquid, and the second layer of ink may not flow with liquid, either, thus displaying a color only, such that the ink may not flow onto the nearby analyte binding area to influence the test result. In the following examples, the second layer-reagent or the second element is a light-emitting element by itself, and located below a nitrocellulose film; such a configuration will not influence the immunoreaction of the analyte binding area, which will be set forth in detail.

In some further embodiments, the colored ink or dye in the positive control area may be directly coated in the detection zone; or, a substance binding to the analyte, for example, an antibody or antigen, is fixed on the detection zone first, after drying, a colored coating, ink or dye is coated on the detection zone, or a colored paper strip is bonded on the detection zone. When the detection zone is located on a film, for example, a nitrocellulose film, a colored second-layer reagent is directly printed, jet printed or coated on the film. The fixed first-layer covered on the second-layer is also achieved in the same way. But these ink will not move with liquid, but be a fixed state.

Figure 10:
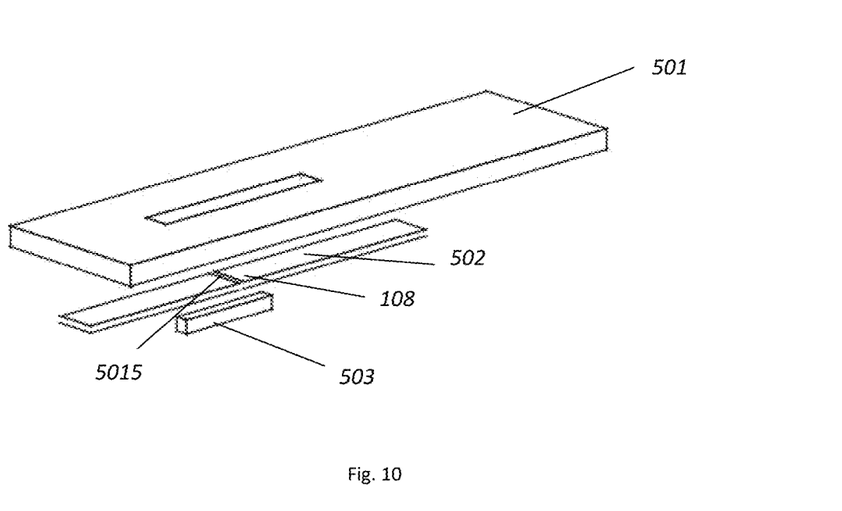
FIG. 10 is a schematic diagram showing a structure in a detailed embodiment of the present invention; the light-emitting element 503 is located below the detection zone as a positive control area; the analyte binding area is located on the detection zone; the test strip is arranged in a box, and the box includes an upper board 501 and a lower board (omitted); the upper board 501 contains a window to display a visual symbol.
Figure 11:
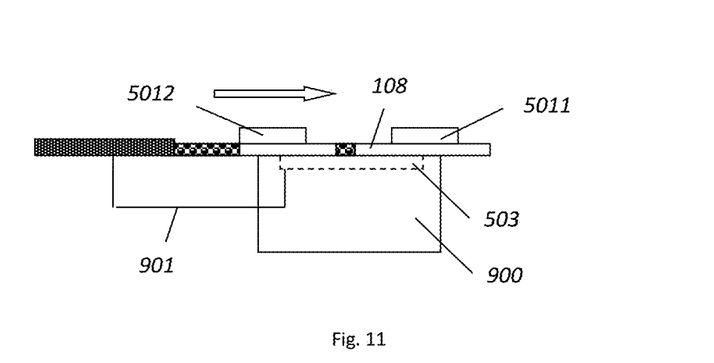
FIG. 11 shows a schematic diagram showing a sectional structure in another detailed embodiment of the present invention.
Figure 12:
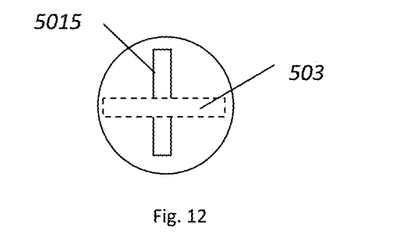
FIG. 12 is a structure diagram showing symbol composition of the detection zone.

In another embodiment, for example as shown in FIGS. 10 and 11-12, the present invention provides a test strip, including an analyte binding area 5015, such as a T line area, which is located on the nitrocellulose film 502. A luminous light source 503 is arranged under the nitrocellulose film, which has a power supply and a light-emitting element, and the light-emitting element is connected to the power supply through a lead wire (FIG. 12). The light-emitting element and the test strip are arranged in longitudinal directions, and combined with the analyte binding area to form a "+"; the light-emitting element has a length of 4-5 mm and a width of 1-2 mm by itself. The positive pole and negative pole (anode and cathode) of the lead wire are connected to a sample application zone, but are not in direct contact with each other; and it is desirable that a current circuit is achieved by a fluid sample. When no test is conducted, the test strip is dry, and the lead wire may not form a current channel, so the light-emitting element will not emit light, or irradiate the film; and the film is dry and not transparent. When a sample is to be tested such as urine, the sample is applied to a sample pad, and at this time, the power is turned on, so the light-emitting element emits light. The light-emitting element itself presents in a certain shape, for example, a rectangle, then the rectangular shape is displayed under the film, for example, a "–" symbol. As the liquid flows continuously, the film becomes transparent when exposed to water, so that the light-emitting elements below is displayed, and the shape can be seen from above the film. Simultaneously, depending on presence of the analyte in the sample, accumulation of symbols may occur or not in the analyte binding area, leading to display of a colored line or not. The line and the shape of the light-emitting element displayed under the film are combined to form a symbol, which indicates a positive or negative result; for example, the combination of a cross "+" indicates a positive result, and a combination of "–" indicates a negative result, a line always shows in the positive control area, and the symbol changes based on presence of a color line in the analyte binding area.

Figure 15:
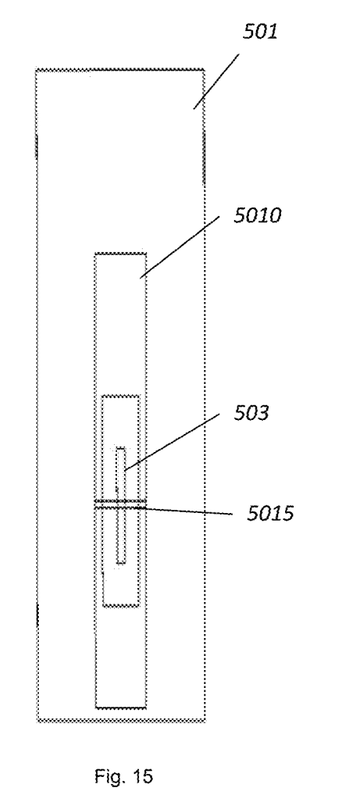
FIG. 15 is a structure diagram showing a principle that a light source is converted into a specific shape in the positive control area.

In some embodiments, a shape of a light-emitting element itself is simply used to directly form a positive control area. To obtain a beautiful and neat symbol, and avoid an incompatible color and shape of the analyte binding area, it is required that the light-emitting element is a regular cuboid and the light emitted is not scattered or dispersed, but relying on the light emitted by the light-emitting element, which is demanding for a stricter requirement on the selection and shape of the light-emitting element. To simply the design and production, and not affect the visual effect of the final symbol, any light source may be taken, for example, any light-emitting element relying on energization. Such kind of light-emitting element has no demand for light, but a conversion element 900 is taken to render the light to be projected on a film or display under a film, or display a shape or pattern correlated to the positive control area. For example, as shown in FIG. 11, a conversion element 900 is provided below a film, and a small groove 905 or hole 906 is opened on the conversion element, and the groove has a depth and a width adaptable to a light-emitting element 503, such that the light-emitting element is fixed in the groove. Meanwhile, a power supply (omitted) and lead wire are mounted, the anode and cathode are respectively connected on the power supply and light-emitting element via the lead wire; another end of the lead wire is overlapped in the sample application zone or other areas of the test strip as long as a electronic current circuit is formed due to the conduction of the fluid sample. A film, for example, a nitrocellulose film is mounted on the conversion element, and the film includes an analyte binding area, and the area is treated with or fixed with an antibody or antigen binding to the analyte or other binding substances (FIG. 12). Further, the area includes an upper board and a lower board (omitted), such that these components are assembled to form the device (FIG. 15).

Figure 13:
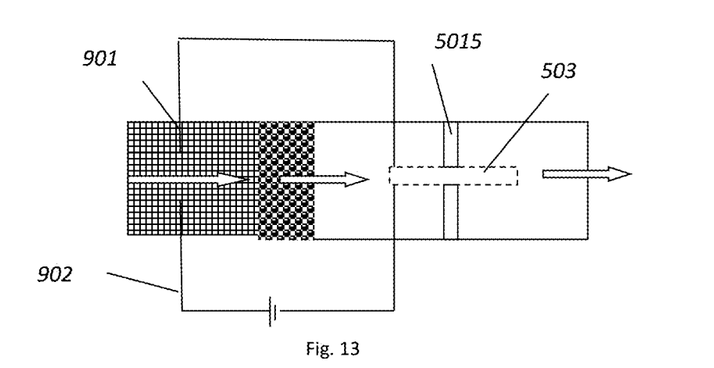
FIG. 13 shows a top view in one embodiment, indicating a schematic diagram before detection.
Figure 14:
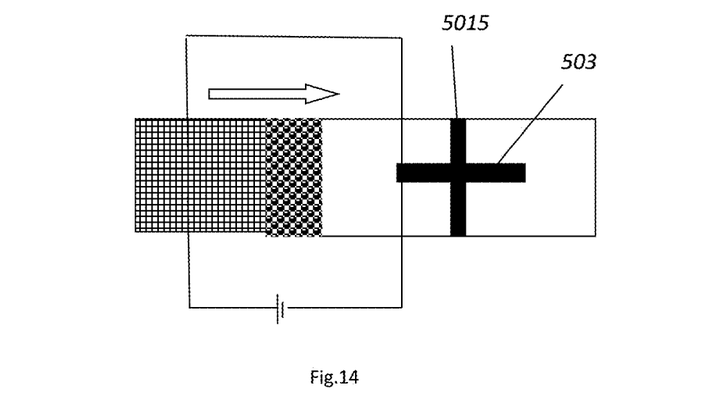
FIG. 14 is a top view in one embodiment, indicating a schematic diagram of a positive result after the detection; in this detailed diagram, the positive control area includes a fine light source at a lower portion of a nitrocellulose film, and when there is an analyte, the light source and the analyte are combined into a symbol showing a positive result.

When no test is conducted, the test strip is dry, and the lead wire may not form a current channel, so the light-emitting element will not emit light, or irradiate the film; and the film is dry and not transparent (FIG. 13). When a sample is to be tested such as urine, the sample is applied to a sample pad, and at this time, the power is turned on, so the light-emitting element emits light. The light-emitting element itself presents in a certain shape, for example, a rectangle, then the rectangular shape is displayed under the film, for example, a "−" symbol. As the liquid flows continuously, the film becomes transparent when exposed to water, so that the light-emitting elements below is displayed, and the shape can be seen from above the film. Simultaneously, depending on presence of the analyte in the sample, accumulation of symbols may occur or not in the analyte binding area, leading to display of a colored line or not. The line and the shape of the light-emitting element displayed under the film are combined to form a symbol, which indicates a positive or negative result; for example, the combination of a cross "+" indicates a positive result (FIG. 14), and a combination of "−" indicates a negative result, a line always shows in the positive control area, and the symbol changes based on presence of a color line in the analyte binding area.

Figure 16A:
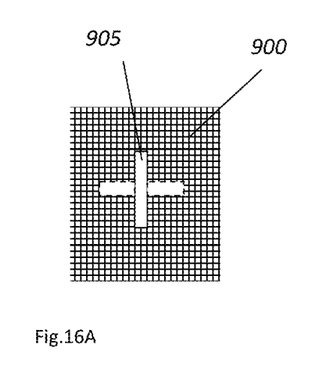
FIG. 16A-16C show a different embodiment that how the light is transferred into the different diagram that is shown the positive control.
Figure 16B:
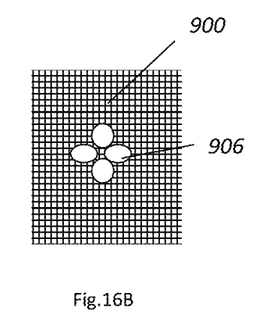
Figure 16C:
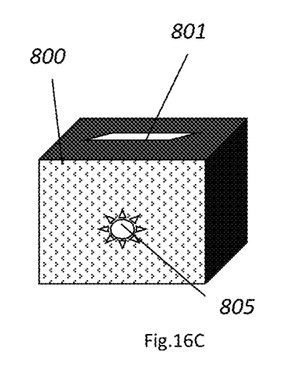

In some embodiments, the conversion element is a box 800; the box is provided with a window 801 or a hollow structure (FIG. 16C); the hollow structure is a shape of the positive control area; the box is provided with a light-emitting element 805, for example, a light bulb, a LED lamp, and the like. The light emitted by these light-emitting elements irradiates after through the window (after being energized); when a film is covered on the surface of the box, the shape of the window will be displayed below the film; and the shape is combined with the analyte binding area on the film to form a recognizable symbol.

The device of the invention can be provided in the form of a test device, featuring a test strip and a holder for holding the test strip, which can be used for specific tests. The holder can be a hollow plastic body with a window located to allow viewing of the detection zone and access to the sample application zone (omitted). In another format, the device is provided as a test strip and no holder is included. The holder can also be located only at one end of the test strip to enable the user to pick it up without contamination of the device, and the sample application zone placed into a sample solution.

In some formats, the device can also include a control line (30), in addition to the positive control area. In these formats, the control line can appear upstream or downstream of the positive control area. A positive result is not only determined by viewing the detection zone for the presence of a recognizable symbol, but also by comparing the analyte binding area to the control line. In some assays, the relative intensities of the two lines are compared to determine a positive or negative result of the assay. In one format of this embodiment, the analyte is luteinizing hormone (LH).

Matrix

In one embodiment, the test strip contains a bibulous material, providing a matrix to support the flow of a liquid. "Matrix" refers to a material that supports the flow and transport of a liquid. In one embodiment, the matrix is a bibulous material. The flow of fluid through the device can be achieved by the force of capillary action. "Bibulous" materials are those that readily absorb liquid and through which liquid is transported by the force of capillary action. Examples of the bibulous materials include nitrocellulose, filter paper, glass fiber, polyester and other suitable materials.

Sample Application Zone

The sample application zone can contain buffer for solubilizing the sample, or can simply be a location on the matrix for the application of sample, but it can also contain other reagents for conducting the assay. For example, the "scavenger" antibodies can be present in the sample application zone, the reagent zone, or other areas of the matrix in those embodiments where they are useful. The sample application zone can therefore also be a reagent zone. Sample is advantageously applied in a liquid form, but can also be dried on the test strip, and the assay begun by applying water, buffer n and other reagents. The sample itself can be a liquid sample or a solid sample that has been liquefied or otherwise prepared in a liquid form.

Reagents

The reagent contained in the reagent zone can be movably present in the reagent zone. Some reagents can be attached to a label and bind to the analyte of interest in the sample to form a labeled analyte. The sample application zone and/or reagent zone may also include a buffer solution for dissolving samples and adjusting pH values necessary for special tests. In one embodiment, the reagent zone contains a specific binding molecule (for example, an antibody or antibody fragment) and is connected to the label. The label can be any suitable one, such as gold sol, fluorescent dye or water-soluble dye. The specific binding molecule can specifically bind to one or more epitopes of the analyte of interest, thereby labeling the analyte.

Detection Zone

The detection zone of the device includes a positive control area, and an analyte binding area. The positive control area is that space located in the detection zone, but is not a part of the positive control area or the analyte binding area. The detection zone may include a negative control area, and the negative control area is located in the detection zone and is neither a part of the positive control area nor a part of the analyte binding area. If a detectable signal from a detectable label is detected in the area, the assay is invalid due to a failed negative control. In some specific embodiments, the detection zone is rectangle or square on a bibulous matrix that encompasses the length of the positive control area and the analyte binding area, measuring longitudinally along a test strip, and is further encompassed by lines extending from the side of the test strip. The detection zone can also have a plastic part placed over it, to provide a viewing window limited within the detection zone. The detection zone is related to all the structures of the device. Thus, structures can be contained in the detection zone whether they are physically located on the matrix, in the matrix or under the matrix, as long as they are visible upon observation of the detection zone in either a dry or wet state, or as a result of a positive or negative analyte assay result.

Symbols

The recognizable symbol is created by the interaction of the positive control and analyte binding areas on the device.

The positive control area can be delineated by a portion of a symbol that will interact with the analyte binding area and affixing the shape to form a recognizable symbol. The symbol can also selected to present one recognizable symbol for a negative result, and another recognizable symbol for a positive result, where the positive control area and the analyte binding area interact to form a recognizable symbol. The symbol can be formed above, below or within the nitrocellulose, or located between the nitrocellulose and a backing for the nitrocellulose film.

In various embodiments, the "recognizable symbol" is a plus sign, a minus sign, a minus sign, a strip, an "X", or another symbol known in the art or in general parlance as conveying a particular meaning that can be associated with the assay result. Any meaningful symbols can be selected, such as a letter from the Roman alphabet, a number, a mathematical operator, a scientific symbol, or a letter from another language like Chinese, Japanese or alphabet, system.

For example, a minus sign is advantageously used to indicate a negative result because it is a meaningful and easily recognized symbol. Other symbols, such as an "X", "O", "zero", "Y", "N", "Z", or an arrow can also be selected. These symbols can be easily read and understood by an untrained user. When one or more components that can change color and the demarcation of the positive control area are selected to be the same color, the recognizable symbol is formed by the interaction of the positive control area and the analyte binding area when a positive result is obtained. When the symbol is a minus sign, it can have either right-angled or rounded edges.

Analyte Binding Area

The analyte binding area is located on the matrix so that it can interact with the positive control area to form a recognizable symbol when the analyte of interest is present in the liquid sample. The labeled reagent present in the reagent zone can bind (directly or indirectly) to the analyte of interest, thereby labeling the analyte of interest with a detectable label as it flows through the matrix. The analyte binding area can also contain a reagent that can bind to a moiety associated with the analyte. The moiety can be an antigenic determinant on the analyte itself or on a reagent bound to the analyte (for example, a reagent that bound to the analyte as it passes through the reagent zone). In various specific embodiments, the reagent bound to the analyte can be an antibody, a fragment thereof or a portion of an antibody, an antibody (or fragment thereof) derived from a species different from the antibody affixed to the analyte binding area, or another component of a specific binding pair, for example, avidin, streptavidin, or biotin, which itself can be bound to a moiety bound to the analyte.

In one specific embodiment, the analyte binding area is located on both sides of the positive control area, so when an analyte is present in a sample, the analyte is labeled and retained in the analyte binding area, and interacts with the positive control area to form a recognizable symbol and indicate a positive test result. In another specific embodiment, the analyte binding area is a strip distributed along the latitude of the longitudinal axis of the test strip, which includes a specific binding molecule of the analyte, or a molecular complex that binds to the analyte. In all examples, when the labeled analyte in the sample flows through the detection zone, it accumulates in the analyte binding area and produces a detectable color in the analyte binding area. The color of the analyte binding area and that of the positive control area interact to form a recognizable symbol. In some specific embodiments, the label is a colored particle, which may be a dextran particle, a gold sol, or other labeled particles, and the labels can be any suitable label providing a detectable signal.

Reagent Zone

The label that binds to the analyte of interest provides an observable detection signal which produces the analyte binding area. When the analyte is present in the sample, it interacts with the positive control area to form a recognizable symbol. The specific binding molecule of the analyte carries the label of the reagent zone. When the specific binding molecule captures the analyte and the labeled analyte binds at the analyte binding area, the area can be observed as with the accumulation of the label. The specific binding molecule of the analyte refers to a binding molecule that binds to the analyte but cannot firmly bind to any other molecules in the sample. The specific binding molecules of the analyte can also bind to the molecules that indicate the presence of the analyte in the sample or have association with the presence of the analyte. Firm binding refers to binding to the extent that it changes the test result or makes the test result not obvious. In some specific embodiments, the specific binding molecule may be an antibody or an antibody fragment (for example, the Fab region of an antibody), an antigen, a receptor or a receptor fragment that binds to a ligand, or a component of a biotin-streptavidin binding pair or other types of binding pairs.

In this way, the reagent zone can provide a label, and when the sample flows through the reagent zone, the analyte binds to the label that can generate a detectable signal. The "labeled area" refers to the part on the matrix that includes the substance marking the presence of the analyte in the sample. Therefore, a reagent zone is a labeled area. The "label" can be any suitable label that produces a detectable signal. For example, the label may be a soluble particle, a fluorescent particle, a chemiluminescent particle, a metal or alloy (for example, colloidal gold), or a capsule, particularly a liposome including visible dyes. Hydrophobic sols are also useful. Hydrophobic organic dyes or pigments are insoluble in water or only a little part thereof is soluble. The label may also be a polymer particle, such as a colored polystyrene particle (spherical). Other useful particulate labels include ferritin, phycoerythrin, phycobilin-protein, precipitated or soluble metals or alloys, fungi, seaweed, or bacterial pigments or derivatives, such as bacterial chlorophyll or other plant raw materials. In some embodiments, the label may be a colored particle, such as a dextran particle. In other specific embodiments, the label and dye of the same color are used as positive control to enhance the interaction between the two signals when a single obvious symbol is generated on or in the matrix.

In other specific embodiments, the label may be a labeled specific binding molecule of the analyte (i.e. an antibody). For example, in one embodiment, the analyte of interest is human chorionic gonadotropin (hCG), and the label binding to hCG is a IgG-Gold anti-hCG antibody. When the sample arrives at the reagent zone (or labeled area), the hCG in the sample is bound by the IgG-Gold anti-hCG antibody. The labeled antibody does not interfere with the binding between the capture molecule in the analyte binding area and the labeled hCG. For example, the label can bind to one part of the analyte, and the capture molecule can bind to the other part of the analyte or the label. The hCG-anti-hCG antibody-gold complex moves downstream of the matrix. When the complex arrives at the analyte binding area, it bind to the capture molecule to form a gold-anti-hCG anti-hCG-anti-hCG antibody. The capture molecule may be another specific binding molecule of hCG, or a specific binding molecule that binds to the moiety of the hCG analyte. When the gold-anti-hCG specific binding molecule-hCG-anti-hCG specific binding molecule complex binds at the analyte binding area, the analyte binding area is colored by the gold label on the complex and the gold label becomes visible to the naked eye in the analyte binding area. In one specific embodiment, the specific binding molecule is an antibody or antibody fragment. The label and capture binding molecules can bind to different epitopes on the analyte. In one embodiment, the labeled specific binding molecule binds to β-hCG, while the capture binding molecule binds to α-hCG.

"Antibody" refers to immunoglobulin, natural or partially or fully synthesized. The term also covers derivatives of the antibodies having the binding ability, as well as any protein including a binding domain that is homologous or largely homologous to the binding domain of an immunoglobulin. The proteins may be derived from natural substances, or partially or fully synthesized. An antibody may be a monoclonal or polyclonal antibody. An antibody may be one of any type of immunoglobulin, including the human immunoglobulin type of IgG, IgM, IgA, IgD, IgG and IgE. An "antibody fragment" is a derivative of an antibody or a portion of an antibody that is less than the full length. The antibody fragment can have at least a significant site of the full-length antibody's binding ability. For example, antibody fragments may include Fab, Fab', F(ab')2, scFv, Fv, dsFv dimer, and Fd fragments, but not only the above.

An antibody fragment may be produced by any ways. For example, an antibody fragment can be produced by enzymatic hydrolysis or chemical degradation of a complete antibody, or by recombination from genes encoding the partial antibody sequences. In other words, the antibody fragment can be partially or completely produced by recombination. The antibody fragment may be any single-chain antibody fragment. In other words, the antibody fragment may include multiple peptide chains that are mutually connected to each other, for example, connected by disulfide bonds. The antibody fragment can also be any type of multi-molecular complex. A functional antibody fragment is generally composed of at least about 50 amino acids, while more antibody fragments may include about 200 amino acids at least.

Single-chain Fvs (scFvs) are recombinant antibody fragments, which is only produced by covalent binding of variable light (VL) and variable heavy (VH) chains by a polypeptide chain. Either $V_L$ or $V_H$ has an amino terminal region. The polypeptide chain is variable in length and composition, and its length can bridge the two variable domains, without any serious effect on the arrangement of atoms. A polypeptide chain is generally formed by extension of glycine and serine residues, and some glutamate and lysine residues are distributed in a scattered way to increase the solubility. "Dimer" refers to a dimer of single-chain Fvs. A monomer of the dimer generally includes shorter peptide chains than most single-chain Fvs, showing a tendency to form dimers.

A "Fv" fragment consists of a VH and a VL domain which are non-covalently connected. The term "dsFv" herein refers to an Fv of an intermolecular disulfide bond including a stable VH-VL pair. A "F(ab')$_2$" fragment refers to the fragment of an antibody, which is essentially the same as the fragment obtained by digesting immunoglobulin (usually IgG) with pepsin at pH 4.0-4.5. The fragment can also be synthesized by recombination. The "Fab" fragment is an antibody fragment, which is essentially the same as the fragment obtained by reducing disulfide bonds on the F(ab')$_2$ fragment with two heavy chains mutually connected. Fab' fragments can also be synthesized by recombination. The "Fab" fragment is an antibody fragment that is essentially the same as the fragment obtained by digesting immunoglobulin (usually IgG) with papain. Fab fragments can also be synthesized by recombination. The heavy chain fragment on the Fab fragment is a Fd fragment.

The user cannot see the analyte binding area before using the device. In one embodiment, according to presence of an analyte in the sample, the test result will be displayed with a "+" sign or a minus sign. When the analyte is not present in the sample, the positive control area will display a minus sign. If the analyte is present in the sample, the analyte reacts with the reagent in the labeled reagent zone and is then captured by the specific binding molecule in the analyte binding area. In one embodiment, the analyte binding area includes two parts located along the latitude of the test strip on both sides of the positive control area. "Latitude direction" refer to the direction that is perpendicular to the direction of the liquid flowing through the device, and also refers to the direction perpendicular to the full length of the test strip. The positive control area and the analyte binding area may interact to form a recognizable symbol. In one embodiment, the positive control area can interact with the analyte binding area to show a plus sign, and the analyte binding area can also interact with the positive control area to form other recognizable symbols.

In another specific embodiment, the analyte binding area is an area crossing the test strip, and the positive control area includes two parts on both sides of the analyte binding area. Therefore, the positive control area refers to the two parts located in the longitude direction of the test strip, and the analyte binding area is located at the top of the positive control area or between the positive control areas. In different specific embodiments, the areas may or may not overlap. One or more components used in the positive control area or on the filament may use the same color, so that the positive control area and the analyte binding area interact to form a single symbol. In this way, the positive test symbol is indicated by a plus sign and the negative test symbol indicated by a minus sign.

In another specific embodiment, a plus sign is formed by the positive control area and the analyte detection zone, which may or may not overlap. In the specific embodiment, the analyte binding area on the test strip is shown first and followed by the positive control area, so that a plus sign is displayed when the test is positive and a minus sign is displayed when the test is negative.

In another specific embodiment, the positive control area is arranged at the side of the test strip, and the analyte binding area is in the direction of longitude. The symbol to indicate a positive result is still a plus sign, and the symbol to indicate a negative result is still a minus sign. Compared with other embodiments, only the difference only lies in position.

In a relevant specific embodiment, the positive control area consists of several aligned bars (not single bars), which are adjacent to and perpendicular to the analyte detection zone, thus to form a plus sign. On the contrary, the analyte binding area may be composed of several aligned bars perpendicular to and adjacent to the positive control region, which together form a plus sign.

In another specific embodiment, the detection zone and the positive control area interact with each other to form an "X". In the specific embodiment, the detection zone and the positive control area are set to form an angle with the flow direction of the sample. In a further specific embodiment, the detection zone and the positive control area are set to interact rightly to form a "Y".

Type of the Analyte

The present invention can be used to analyze any analyte. The analytes that can be stably detected by the present invention include (but not only include) human chorionic gonadotropin (hCG), luteinizing hormone (LH), ovarian stimulating hormone (FSH), hepatitis C virus (HCV), hepatitis B virus (HBV), hepatitis B surface antigen, HIV and any abused drug. The analyte can be detected in any liquid or liquid sample, including urine, saliva, saliva, blood, plasma, or serum.

There are also other examples of analyte, such as muscle ammonia acid anhydride, bilirubin, nitrite, protein (nonspecific), blood and white blood cells, blood sugar, heavy metals and toxins, bacteria components (for example, certain types of bacteria of special proteins and sugars, like *E. coli* 0157: H7 and *Staphylococcus aureus, Salmonella*, gas capsule *Clostridium, Campylobacter*, hyperplasia of monocyte *Listeria*, enteritis *Vibrio*, or wax-like *Bacillus*). Any other analyte suitable for the lateral flow test may be detected by the device.

Type of Samples

Any type of sample can be tested by the device of the present invention, including body liquids (such as urine and other body liquids, as well as clinical samples). Liquid samples may be derived from solid or semi-solid samples, including feces, biological tissue and food samples. The solid and semi-solid samples may be converted to liquid samples by any appropriate means, for example, mixing, crushing, soaking, incubating, dissolving in an appropriate solution, or enzymolysis of solid samples (e.g. water, phosphate buffer, or other buffer). "Biological samples" include samples from live animals, plants and food, and also include urine, saliva, blood, and blood composition, cerebrospinal liquid, vaginal swabs, semen, excrement and urine and sweat, secretions, tissues, organs, tumor, tissue and organ cultures, cell cultures and the conditioned media, regardless of a man or an animal. Food samples include processed food compositions and finished products, meat, cheese, wine, milk and drinking water. Plant samples include samples derived from any plant, plant tissue, plant cell culture and conditioned media therein. "Environmental samples" refer to the samples that are derived from the environment (e.g. a sample of lake water or other water bodies, sewage, soil, groundwater, seawater, waste water). Sewage and associated wastes may also be included in environmental samples, and plant samples include samples from any plants, plant tissues, plant cell cultures and media.

Use Method

The present invention also provides a method for detecting the presence of an analyte in a liquid sample with a device of the present invention. The method includes the following steps: placing a liquid sample on the sample application zone of the device; and then making the liquid sample flow through the test strip. The liquid sample is placed on the sample application zone in any simple and feasible method, for example, a dropper.

After the liquid or liquefied sample is added to the sample application zone, the sample flows through the matrix and enters into the reagent strip. The reagent required for the test and/or marking the analyte interacts with the sample after the sample enters into the reagent zone. Hence, the analyte in the sample is labeled with a detectable label, and the analyte here is an antibody carrying a gold-sol particle of the analyte. As the sample flows through the device, the analyte in the liquid sample is labeled with a detectable label and kept in the analyte binding area of the detection zone. The analyte binding area includes a component of a moiety of the specific binding pair associated with the analyte, and the analyte here is an antibody that binds directly to the epitopes of the analyte. In addition, the colorless reagent on the positive control area becomes transparent when exposed to water, showing the colored area; or, after electrification, the light emitted by the light source is projected onto the positive control area, so that the positive control area shows the color, i.e. red.

The positive control filaments and the detectable label may use the same color, so that when the labeled analyte binds at the analyte binding area, the interaction between the positive control area and the analyte control area produces a recognizable label in the detection zone, which is a plus sign here. In the example, when the gold-sol accumulates in the analyte binding area, it shows red, and it can interact with the red positive control filament to form a plus sign.

In the absence of analyte in the sample, the initial symbol (a minus sign in positive control area) is clearly visible in the detection zone, and a minus sign is displayed in the detection zone at the end of the test to indicate a negative result.

Test Kit

The present invention also provides a kit for detecting a presence of an analyte in a liquid and a user manual of the device. The kit of the present invention can be packaged into any form according to the customer's requirement.

In one embodiment, the test strip can be designed to a device for "mid-stream urine" fertility test, which includes a box to place a test strip; and a yarn; wherein the yarn can associate with the sample application zone on the reagent strip and the liquid reagent used to detect the target fertility hormone liquid, such as human chorionic gonadotropin (hCG), luteinizing hormone (LH) or ovarian stimulant (FSH). A window is set on the box beside the detection zone to observe the test result. In some specific embodiments, a kit device for a mid-stream urine pregnancy test includes one or more independently packaged devices and a user manual. The user manual describes how to conduct the test and explain the results. For example, a patient provides a urine sample at the sample collection point of a urine testing device, which transports the urine to the sample application zone of the device, and the liquid flows through the reagent zone and the detection zone of the device. If the test result is negative (no pregnancy), the discoloration component in the positive control area is wetted by the assay fluids and turns to a second color, showing a minus sign. If the test result is positive (pregnancy), the discoloration component of the positive control area interacts with the color of the analyte binding area to form a plus sign.

In all the specific embodiments, the kit includes 4 or more or 6 and above ovulation devices, 1 or more pregnancy test devices, and a user manual, wherein the user manual describes how to use the device to determine the peak time of luteinizing hormone and how to use the device for pregnancy test. The device may be any of the specific embodiments described herein. The device may also be designed as a "test strip" used in a professional laboratory.

In another specific embodiment, the kit may include a test strip of the present invention. In one embodiment, the test strips may be designed as test strip for pregnancy test packaged in a box containing 15 or 20 or more test strips and a user manual.

In the absence of any element or limitation specifically disclosed herein, the invention shown and described herein may be achieved. Terms and expressions herein are used as descriptive terms and not as a limitation, it's not intended to exclude any equivalent of characteristics or a part of them shown and described in use of these terms and expressions, and it should be recognized that all modifications are feasible within the scope of the present invention. It should therefore be understood that, although the present invention has been specifically disclosed through various embodiments and optional characteristics, modifications and variations of concepts described herein may be employed by ordinary technicians skilled in the art, and these modifications and variations are considered to fall within the scope of the present invention defined by the attached claims.

The content of articles, patents, patent applications and all other documents and electronically available information described or documented herein is incorporated in the full text to some extent for reference, as if each individual publication is specifically and individually pointed out for reference. The applicant reserves the right to keep any and all materials and information from any such articles, patents, patent applications or other documents into the present application.

The invention claimed is:

1. A device for indicating a test result of a specimen using recognizable symbols, comprising a reagent strip, wherein the reagent strip comprises a detection zone including an analyte binding area and a positive control area, wherein the positive control area comprises a first element and a second element, wherein the second element is colored, and the first element is not transparent when dry but becomes transparent when wetted, wherein the second element is a light-emitting element, and the light-emitting element emits light after a current circuit of the light-emitting element is formed by conduction of a liquid sample.

2. The device according to claim 1, wherein the analyte binding area and the positive control area are combined into a symbol to display the test result.

3. The device according to claim 2, wherein when the liquid sample includes an analyte, the combination is a positive symbol to indicate a positive result; when the liquid sample does not contain the analyte, the combination is a negative symbol to indicate a negative result.

4. The device according to claim 3, wherein the positive symbol is "+", and the negative symbol is "−".

5. The device according to claim 3, wherein the analyte binding area comprises a fixed antibody, and the antibody may directly or indirectly bind to the analyte.

6. The device according to claim 5, wherein the analyte comprises HCG or LH.

7. The device according to claim 5, wherein the device further comprises a reagent zone located on the upstream of the detection zone, and the zone comprises a labeled reagent flowing with liquid, and the labeled reagent comprises a specific antibody having a colored particle and the analyte.

8. The device according to claim 7, wherein the device further comprises a sample application zone for receiving a fluid the liquid sample, and the sample application zone is located on the upstream of a reagent zone.

9. The device according to claim 1, wherein the first element becomes transparent from a non-transparent state to show the second element.

10. The device according to claim 1, wherein the first element is covered on the second element.

11. The device according to claim 1, wherein the first element is an ink reagent, and the ink reagent is not transparent when dry but becomes transparent when wetted.

12. The device according to claim 1, wherein the first element is a film element, and the film element is not transparent when dry but becomes transparent when wetted.

13. The device according to claim 1, wherein the second element will not change in color when wetted.

14. The device according to claim 1, wherein the second element is red or blue.

15. The device according to claim 1, wherein the downstream of the detection zone comprises a test result control zone, used for indicating whether the test result is valid.

16. The device according to claim 1, wherein the analyte binding area and the positive control area are located on a nitrocellulose or nylon film.

17. A device for indicating a test result of a specimen using recognizable symbols, comprises a reagent strip, the reagent strip comprises a detection zone including an analyte binding area and a positive control area, and the positive control area includes a light-emitting element which emits light after energizing, the light emitted by the element is projected to the positive control area, thereby combining with the analyte binding area to form a symbol to indicate the test result.

18. The device according to claim 17, wherein the light-emitting element emits light after a current circuit of the light-emitting element is formed by conduction of a liquid sample.

19. The device according to claim 17, wherein the light emitted by the light-emitting element penetrates through a conversion element and projects to the positive control area.

20. The device according to claim 17, wherein the device comprises a film, and the analyte binding area and the positive control area are located on the film.

21. The device according to claim 20, wherein the film is not transparent when dry but becomes transparent or substantially transparent when wetted.

22. The device according to claim 17, wherein when an analyte is present in a sample, the combination is a positive symbol to indicate a positive result; when the analyte is not present in the sample, the combination is a negative symbol to indicate a negative result.

23. The device according to claim 22, wherein the positive symbol is "+", and the negative symbol is "−".

24. The device according to claim 23, wherein the conversion element comprises a groove, and the groove is provided with a light-emitting element, or the conversion element is a box structure; the box comprises a light-transmitting window, and a light bulb is arranged in the box; after the light bulb is energized, the light transmits through the window and is projected to the detection region to form the positive control area.

* * * * *